US00PP15420P3

(12) United States Plant Patent
Layt

(10) Patent No.: US PP15,420 P3
(45) Date of Patent: Dec. 14, 2004

(54) ***LOMANDRA* PLANT NAMED 'LM300'**

(50) Latin Name: *Lomandra longifolia*
Varietal Denomination: LM300

(75) Inventor: Todd Anthony Layt, New South Wales (AU)

(73) Assignee: Versascapes, LLC, Mt. Pleasant, SC (US)

( * ) Notice: Subject to any disclaimer, the term of this patent is extended or adjusted under 35 U.S.C. 154(b) by 3 days.

(21) Appl. No.: 10/402,494

(22) Filed: Mar. 28, 2003

(65) Prior Publication Data

US 2003/0233692 P1 Dec. 18, 2003

Related U.S. Application Data

(60) Provisional application No. 60/368,198, filed on Mar. 28, 2002.

(51) Int. Cl.[7] ..... A01H 5/00
(52) U.S. Cl. ..... Plt./263
(58) Field of Search ..... Plt./263

(56) References Cited

PUBLICATIONS

Australian Government Department of Agriculture, Fisheries and Forestry, Database entry for Australian Plant Breeders Right Application No. 2001/092 for 'LM300.' http://www.affa.gov.au/content/pbr database/plant detail.cfm?AID=193762.

"Fine leaf dwarf *Lomandra longifolia*; 'LM300'," Copyright Abulk Jan. 2002.

Gazette entry (Part II) for 'LM300' (Australian Plant Breeders Right Application No. 2001/092), *Plant Varieties Journal* 15:3 (2002).

*Primary Examiner*—Anne Marie Grunberg
*Assistant Examiner*—June Hwu
(74) *Attorney, Agent, or Firm*—Myers Bigel Sibley & Sajovec, P.A.

(57) ABSTRACT

A new and distinct variety of *Lomandra longifolia* plant, designated 'LM300', is characterized by a fine, narrow leaf blade, and compact habit as compared with other varieties of *Lomandra longifolia*. 'LM300' is further characterized by a yellow green to deep-green leaf blade color with greyed orange to greyed purple basal shoots. In addition, 'LM300' is cold tolerant with excellent color retention as compared with other varieties of *Lomandra longifolia*.

5 Drawing Sheets

RELATED APPLICATION INFORMATION

This application claims the benefit of U.S. Provisional application Ser. No. 60/368,198 filed 28 Mar. 2002, the disclosure of which is incorporated herein by reference in its entirety.

Latin name of the genus and species: The Latin name of the novel variety disclosed herein is *Lomandra longifolia.*

Variety denomination: The inventive variety of *Lomandra* disclosed herein has been given the variety denomination 'LM300'.

BACKGROUND OF THE INVENTION

The present invention relates to a new and distinct variety of perennial *Lomandra longifolia,* which has been named 'LM300'. *Lomandra* are a genus of ornamental grass-like plants. The variety 'LM300' was discovered in a nursery in April 1998 in the state of New South Wales, Australia, during a routine inspection of large quantities of cultivated *Lomandra longifolia* 'Katrinus' (unpatented in the United States; Australian Plant Breeders Rights Application No. 1997/168) production stock. 'LM300' is believed to be an "off type" or sport (whole plant) of *Lomandra longifolia* 'Katrinus', due to its much finer leaf and compact size as compared with *Lomandra longifolia* 'Katrinus'. The new variety 'LM300' was first propagated asexually by division in August 1999 in the state of New South Wales, Australia, and has since been asexually propagated by division and tissue culture. The distinctive characteristics of the inventive variety are stable from generation to generation; clones of the variety produced by asexual reproduction maintain the distinguishing characteristics of the original plant.

'LM300' has a compact habit and a narrow leaf forming an attractive ornamental grass-like plant, unlike its parent, which is characterized more as a strapy leaf plant.

An application for plant breeders' rights with respect to 'LM300' has been lodged with the Australian Plant Breeders Rights Office, and was first gazetted in August 2001 (under Application No. 2001/092).

SUMMARY OF THE INVENTION

'LM300' is a distinctive variety of *Lomandra longifolia,* which is characterized by its combination of color, compact growth habit, and fine narrow leaf blade as compared with other varieties of *Lomandra longifolia.* It is a short, rhizomatous plant forming a compact tussock (FIG. 8). The inventive 'LM300' variety has a dwarf and more compact growth habit, and leaves which are finer and narrower, as compared with *Lomandra longifolia* 'Katrinus', *Lomandra longifolia* 'Cassica' (unpatented in the United States; Australian Plant Breeders Rights Application No. 1997/166), or common *Lomandra longifolia. Lomandra longifolia* 'LM400' (pending U.S. Plant patent application Ser. No. 10/626,680; Australian Plant Breeders Rights Application No. 2001/090) also has a fine, narrow leaf blade and compact growth habit; however, 'LM300' may be distinguished from 'LM400' in that it has a greener leaf, a less spiky flower spike, and is more compact in habit than 'LM400'. 'LM300' also exhibits cold tolerance with excellent color retention.

DETAILED BOTANICAL DESCRIPTION OF THE VARIETY

Figure 1:
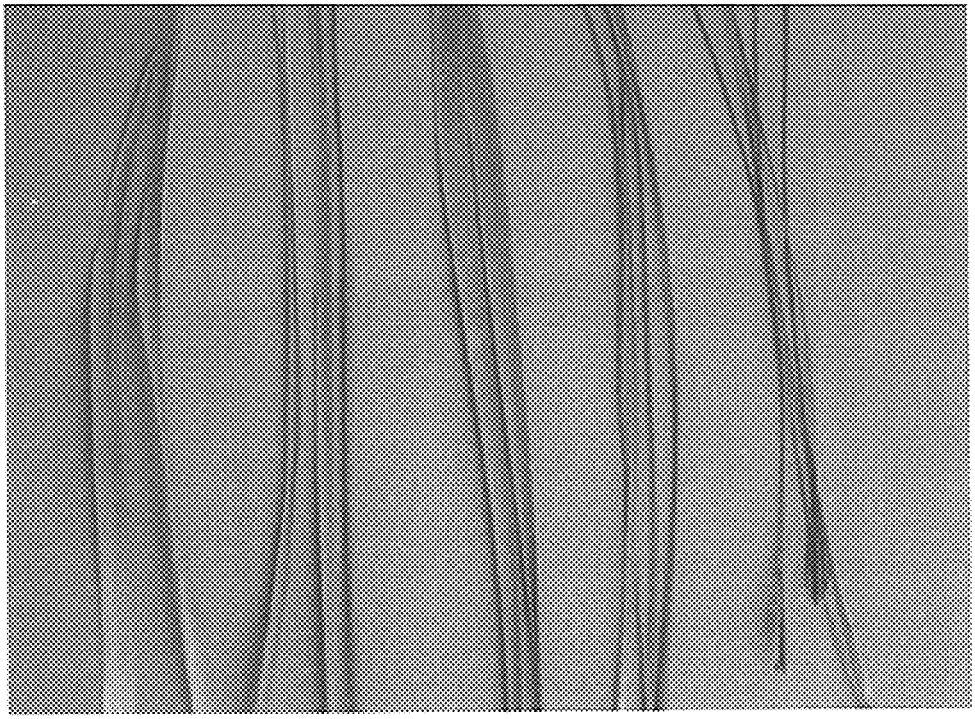
FIG. 1 shows a comparison in leaf width of 'LM300' with several known varieties of *Lomandra longifolia* plants, from left to right, common *Lomandra longifolia,* 'Katrinus', 'Cassica', 'LM400' and 'LM300'.

The following is a detailed botanical description of a new and distinct variety of *Lomandra longifolia* known as 'LM300', based upon observations of the plant grown in nursery pots and field plots in New South Wales, Australia, unless otherwise indicated. The data presented in Tables 1–3, below, were obtained from mature plants that were approximately eighteen-months old on Jul. 6, 2001 when the trials commenced. Other quantitative measurements and color descriptors set forth in the Technical Description of the Variety below were obtained during summer-autumn 2004 from approximately eighteen-month old plants grown in 200 mm pots in Sydney, New South Wales, Australia.

Those skilled in the art will appreciate that certain characteristics will vary with older or, conversely, with younger plants. 'LM300' has not been observed under all possible environmental conditions. Where dimensions, sizes, colors and other characteristics are given, it is to be understood that such characteristics are approximations or averages set forth as accurately as practicable. The phenotype of the variety may differ from the descriptions herein with variations in the environment such as season, temperature, light intensity, day length, cultural conditions, and the like. Color notations are based on The Royal Horticultural Society Colour Chart, The Royal Horticultural Society, London, 1995 edition.

'LM300' is a perennial, dioecious, vegetatively propagated *Lomandra longifolia* plant, and is believed to be an "off type" or sport (whole plant) of *Lomandra longifolia* 'Katrinus'. 'LM300' is a narrow-bladed compact plant, which is unusual for *Lomandra longifolia,* as these plants are usually medium- to wide-bladed strapy plants, and are larger in overall size than 'LM300'. A description of the distinguishing characteristics of 'LM300' and comparisons with other varieties of *Lomandra longifolia* are provided in the accompanying figures, in Tables 1–3, and in the discussion below.

Technical description of the variety:

*Plant characteristics.*—Growth habit upright, height short, distal weeping present, proliferation rhizomatous, depth of rhizomes deep.

*Height.*—Average plant height is 55 cm.

*Spread.*—Average plant spread is 60 cm.

*Leaves.*—Color yellow green (RHS 147B), surface glabrous, attitude upright, apex indentation present, number of predominant indentation two, length of blade long (mean 557.5 mm), width of blade very narrow (mean 3 mm) for this species, rigidity non-stiff (flexible), texture non-coriaceous, curvature concave to convex near base and nearly flat at apex (generally thickened and more incurving on the right hand abaxial edge). The leaf blade is generally a uniform width from base to the tip, with the jagged tip typical of *Lomandra longifolia.*

*Leaf venation.*—The leaf venation pattern is parallel; color is the same as the rest of the leaf.

*Basal sheath.*—Color greyed orange (RHS 166A to 166C), distally tapering, usually tattered.

*Basal shoots.*—Texture fine, width narrow, attitude upright, arrangement cluster. The overall basal shoot color is greyed orange (RHS 166A) to greyed purple (RHS 183B).

*Rhizome.*—Very short (4.5 cm to 6.5 cm); rhizome color with the leaf sheath removed is white (RHS 155C); surface texture of the rhizome is smooth.

*Inflorescence.*—Branching present (generally 2 at nodes), arrangement whorled, shape of scape in cross-section oval at base and rectangular distally. The predominant color of the inflorescence (flower spike) at anthesis is yellow (RHS 13C) with an average length of 195 mm, and an average width of 25 mm. The flower spike is non-spiky to touch, which is unusual for this species.

*Floret length.*—The average length of the floret is 3.3 mm.

*Floret bud.*—The average length of the floret bud is 3 mm; bud shape is oval; color is greyed purple (RHS 183C).

*Pedicels.*—Absent; the florets are sessile.

*Bracts.*—Color transparent to greyed brown (approximately RHS 199D), base of bracts often changes to greyed purple (RHS 183A), position of bracts at the base of each flower cluster, average length of bracts is 50 mm, which is longer than flower cluster, bracts are sharply pointed.

*Flowers.*—Color of outer perianth is greyed purple (RHS 183C) proximally, yellow green (RHS 146A-B) distally along the central zone, and greyed yellow (RHS 161D) along each perianth segment margin; color of inner perianth is yellow (RHS 13C) fading towards the margin to yellow (RHS 13D).

*Flower rachis.*—Average length is 110 mm.

*Flowering period.*—The primary flowering period is in the spring with secondary flowering occurring in summer to autumn in Sydney, New South Wales, Australia.

*Lastingness of bloom.*—Approximately 9 days in summer in Sydney, New South Wales, Australia.

*Fragrance.*—Fragrance is typical of the species, and of medium strength.

*Reproductive organs of male florets.*—Six stamens, anther size is 0.5 mm to 0.8 mm in length, anther color is yellow (approximately RHS 8B).

*Roots.*—Similar to other *Lomandra longifolia,* 'LM300' has a massive root structure.

These and other features and characteristics of 'LM300' are apparent from the figures provided herein.

The growth and morphology of 'LM300' is further characterized in Table 1, which presents data regarding leaf blade width, blade length, leaf color, flower spike length, 'spikiness' of the flower spike, and compactness.

Figure 9:
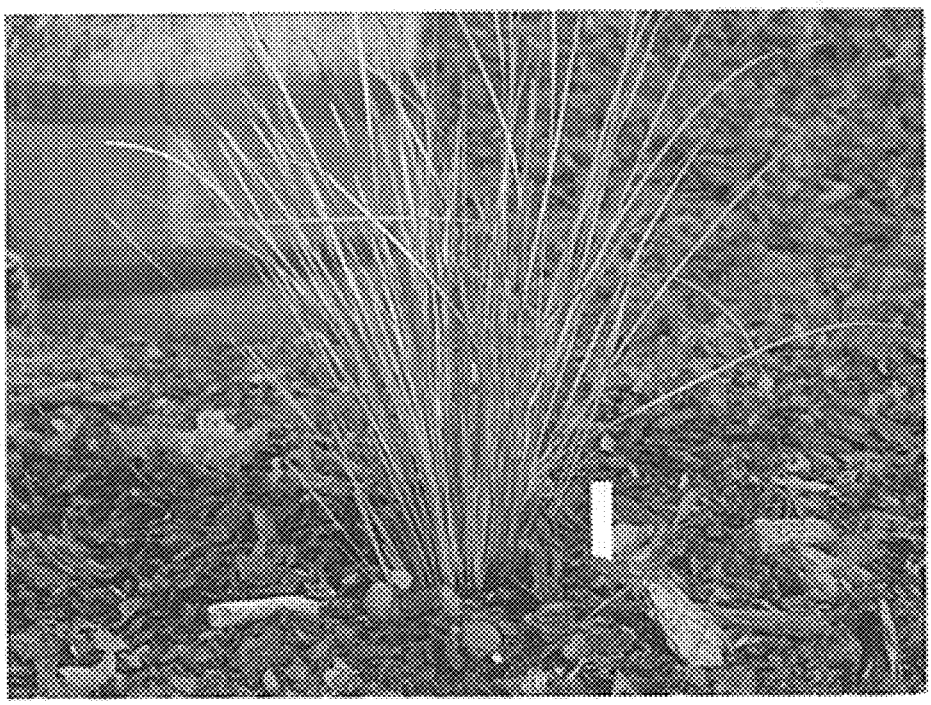
FIG. 9 and FIG. 10 show a 'LM300' plant in a landscape north of Atlanta, Ga. after a temperature of 16° F. (−8.9° C.) was recorded.
Figure 10:
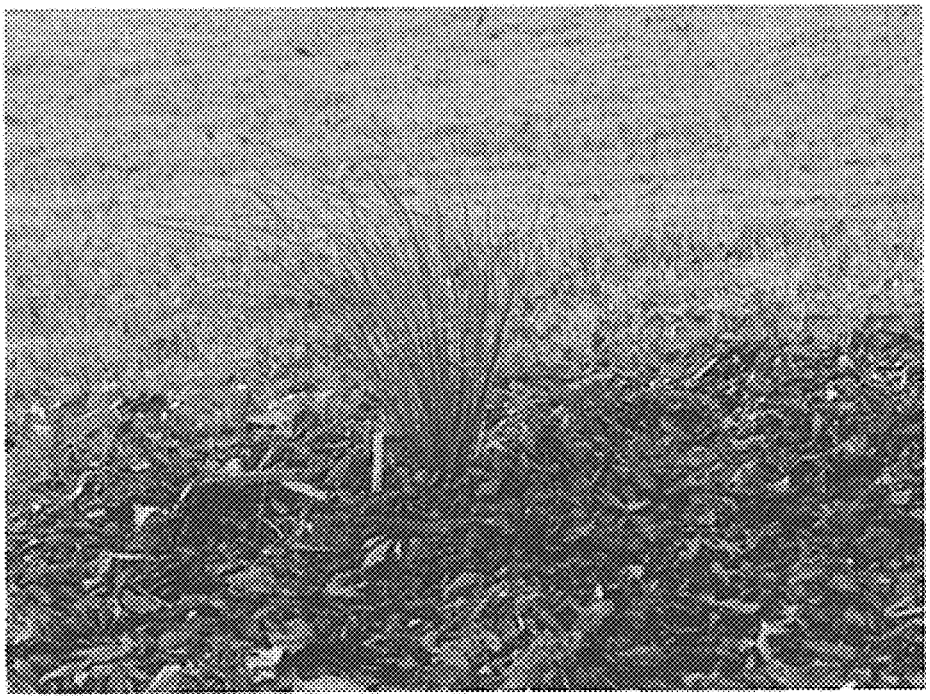

Environmental tolerances: 'LM300' has shown potential for shade tolerance and further shade tolerance tests are underway. 'LM300' has excellent color retention in winter as compared with other varieties of *Lomandra longifolia*. The winter hardiness of 'LM300' is at least to Zone 7b in the Southeastern United States, and evaluation of winter hardiness is ongoing. 'LM300' has been observed to hold color to 6° F. (−14.4° C.). FIGS. 9 and 10 show a 'LM300' plant growing in the landscape north of Atlanta, Ga. after a temperature was recorded of 16° F. (−8.9° C.). The plant shows good color retention, and other dormant grasses can be seen in the background. Winter color retention is also the subject to ongoing tests.

'LM300' has excellent drought tolerance, most likely due to the massive deep root system. 'LM300' has been noted to recover with watering, even after severe wilting.

'LM300' can grow in most soil types, including sandy, clay, alkaline or acidic soils.

'LM300' has been evaluated in the Southeastern United States from North Carolina to Florida and as far west as Texas and performs well under a variety of environmental conditions including high and low temperatures, high humidity, drought and wet conditions. This combination of features is unusual for *Lomandra*; in particular, most *Lomandra* do not perform well under high humidity, wet conditions or low temperatures.

TABLE 1

| Species | Blade Width | Basal Shoot Membrane | Blade Length (Av. length only) | Color |
|---|---|---|---|---|
| 'LM300' | 2.5 to 3.5 mm | Greyed-Orange to Grayed-Purple | 557.5 mm | Yellow-Green |
| 'LM400' | 3 to 5 mm | White/Green & Light Brown | 714 mm | Blue/Grey |
| 'Katrinus' | 7 to 10 mm | Purple | 947.5 mm | Green |
| 'Cassica' | 10 to 15 mm | White/Green | 1095 mm | Blue/Grey |
| Common *Lomandra** | 10 to 16 mm | Variable | 1085 mm | Green-Blue/Grey |

| Species | Flower Spike Length (Av. length only) | Flower Spike Width (Av. length only) | Spikiness |
|---|---|---|---|
| 'LM300' | 195 mm | 25 mm | Very Little Spikiness |
| 'LM400' | 185 mm | 25 mm | Medium Spikiness |
| 'Katrinus' | 240 mm | 65 mm | Medium to Very Spiky |
| 'Cassica' | 230 mm | 48 mm | Very Spiky |
| Common *Lomandra** | 240 mm | 51 mm | Very Spiky |

*Not subject to Australian Plant Breeders Rights

Reference: Test Plots located at Abulk Nursery in Windsor, New South Wales, AUSTRALIA. Planted by Abulk Pty Ltd on July 6, 2001.

Disease resistance and susceptibility: 'LM300' has a good resistance to root rot as compared with other *Lomandra longifolia*.

Comparisons with other *Lomandra longifolia*: 'LM300' may be readily distinguished from other varieties of *Lomandra longifola*.

Figure 2:
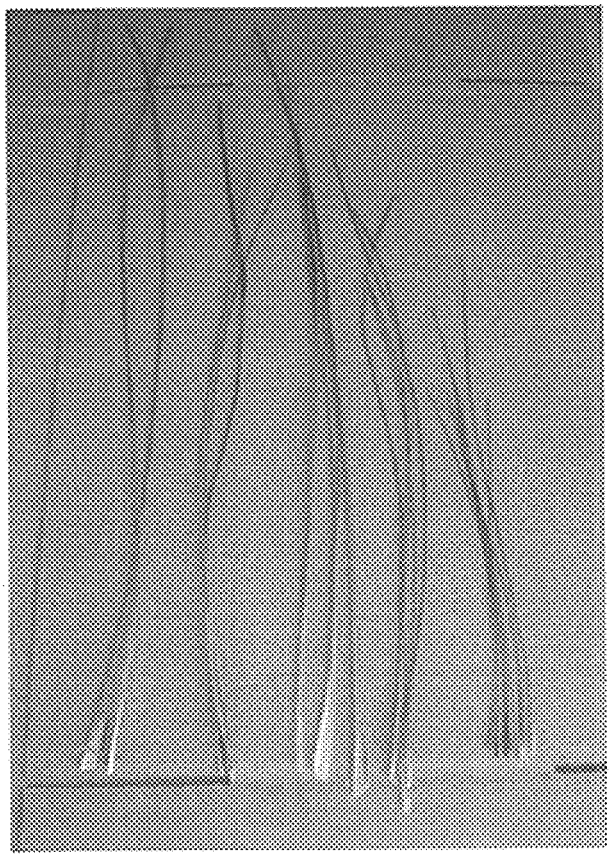
FIG. 2 provides a comparison of the length of the leaf of 'LM300' with several known varieties of *Lomandra longifolia* plants, from left to right, common *Lomandra longifolia,* 'Katrinus', 'Cassica', 'LM400' and 'LM300'.
Figure 3:
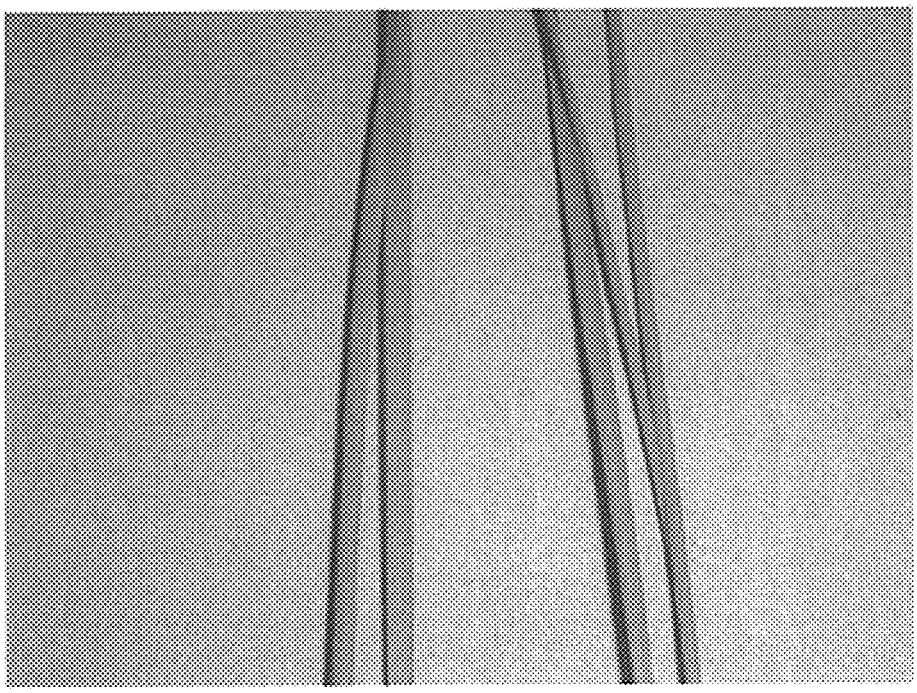
FIG. 3 demonstrates the somewhat finer and narrower leaf of 'LM300' (right) as compared with 'LM400' (left).

The leaf blade width of 'LM300' is finer and narrower than *Lomandra longifolia* 'Katrinus' and other *Lomandra longifolia* (FIGS. 1 and 2). 'LM400' is also a fine-bladed *Lomandra*, but has a somewhat wider leaf blade than 'LM300' (FIGS. 1, 2 and 3).

'LM300' has a more compact habit than *Lomandra longifolia* 'Katrinus', *Lomandra longifolia* 'Cassica' and other common forms of *Lomandra longifolia*.

Figure 7:
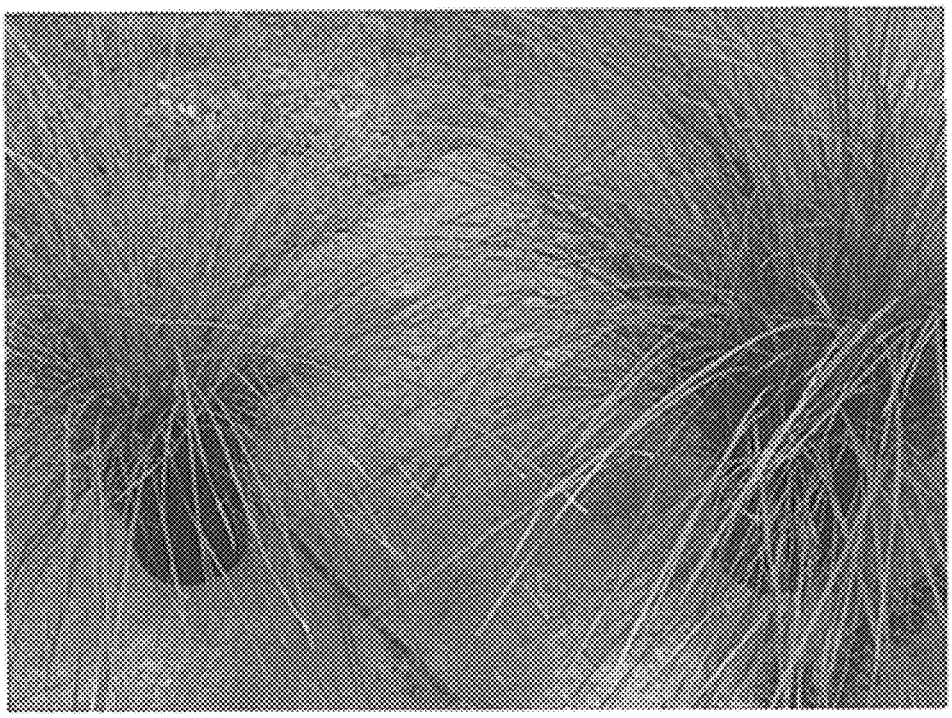
FIG. 7 shows a comparison between 'LM300' (left) and 'LM400' (right) plants.
Figure 8:
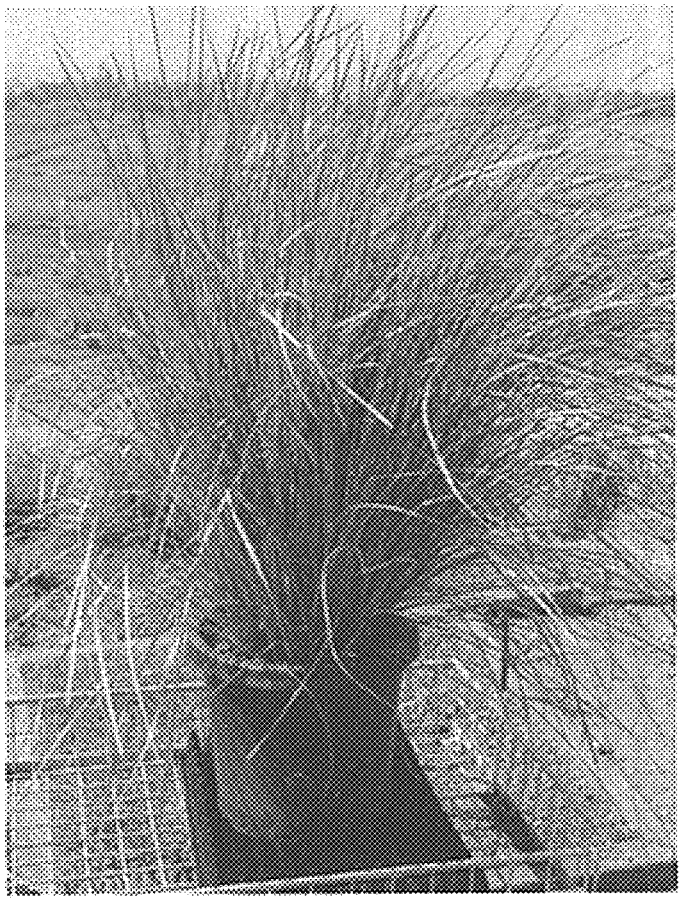
FIG. 8 shows a 'LM300' plant grown in a one-gallon pot.

*Lomandra longifolia* 'LM400' also has a narrow blade and a compact habit. 'LM300' may be distinguished from 'LM400' in that 'LM300' has a greener leaf color (FIG. 7), a less spiky flower spike, and a more compact growth habit.

Figure 4:
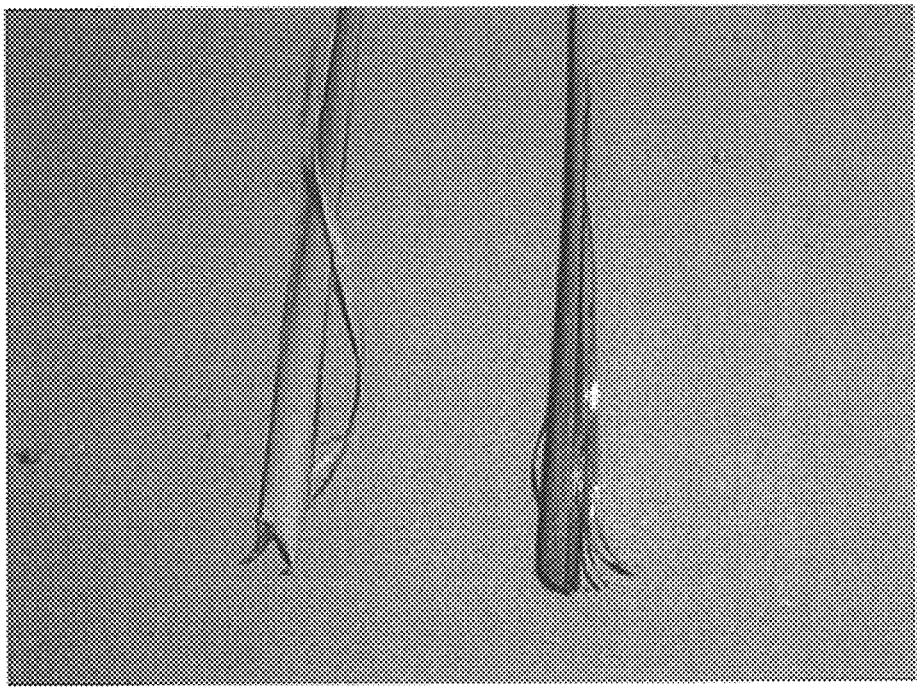
FIG. 4 shows a comparison between the basal shoots of 'LM400' (left) and 'LM300' (right).
Figure 6:
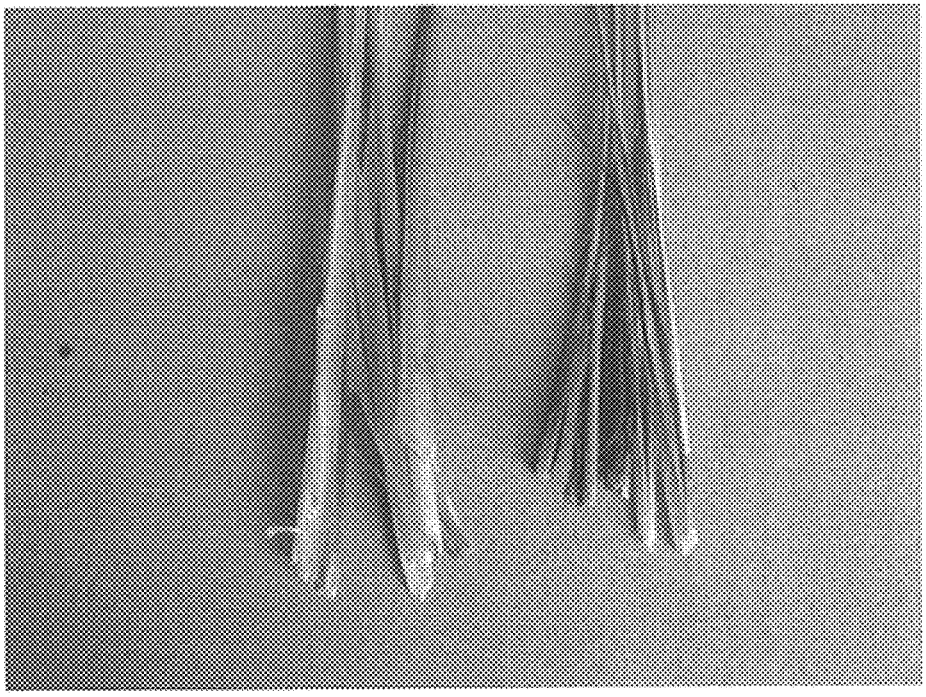
FIG. 6 shows another comparison between the basal shoots of 'LM400' (left) and 'LM300' (right).

The leaves of most *Lomandra* are a grey-green to grey-blue color. In contrast, 'LM300' is yellow green to deep-green in color. In addition, the basal shoots of 'LM300' are greyed orange to greyed purple, similar to 'Katrinus' which has purple basal shoots (FIGS. 4 and 6). In contrast, 'LM400' has grey-blue leaf color and white-green or light brown basal shoots.

'LM300' has a flower spike, which is not spiky to touch, whilst the flower spike of *Lomandra longifolia* 'Katrinus' and *Lomandra longifolia* 'Cassica' are relatively spiky to touch. 'LM300' is also less spiky to touch than 'LM400'.

Figure 5:
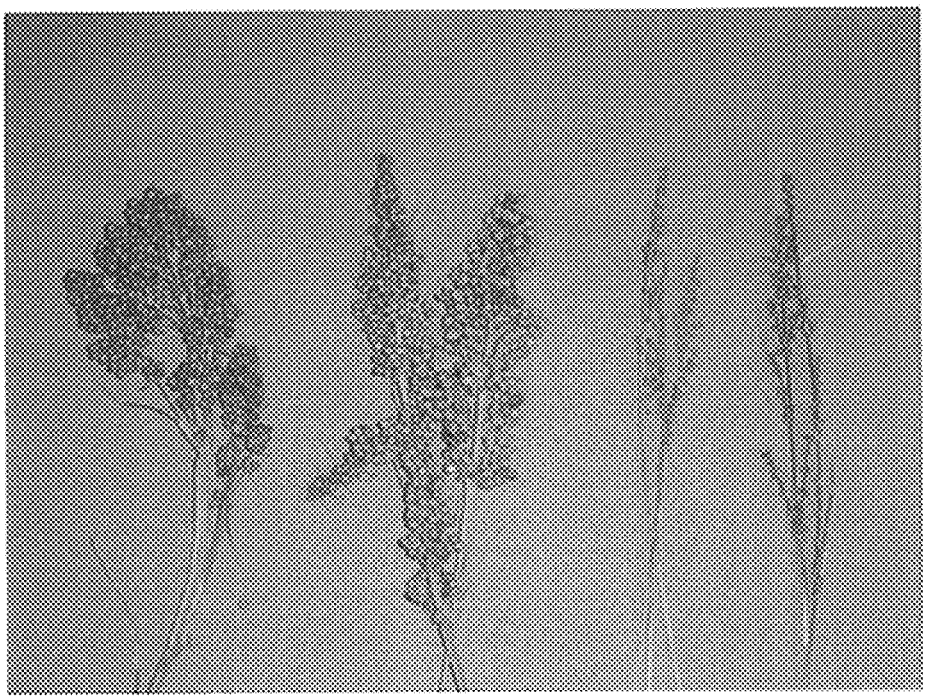
FIG. 5 provides a comparison of the seed head of 'LM300' with several known varieties of *Lomandra longifolia* plants, from left to right, 'Katrinus' 'Cassica', 'LM400', and 'LM300'.

'LM300' has a smaller flower spike than *Lomandra longifolia* 'Katrinus' and *Lomandra longifolia* 'Cassica'. The flower spike of 'LM300' is similar to that of 'LM400' in size. Thus far, 'LM300' has not been observed to produce viable seed, whilst *Lomandra longifolia* 'Katrinus', 'Cassica' and most other known *Lomandra longifolia* produce viable seed from the female plant (FIG. 5). Like 'LM300', 'LM400' does not appear to produce viable seed.

Asexual reproduction: After its initial discovery, 'LM300' was transplanted into a 140 mm pot for further trials and testing. After divisions were made for several subsequent generations, 'LM300' was observed to retain the color, size and fine leaf characteristics that were originally noted in the parent plant. 'LM300' was then divided into many larger pots for further evaluation. 'LM300' has also been asexually propagated using tissue culture techniques.

During these divisions, it was noted that 'LM300' can produce 7 to 10 divisions per 140 mm pot, as compared with 2 to 5 divisions for *Lomandra longifolia* 'Katrinus', *Lomandra longifolia* 'Cassica' and common *Lomandra longifolia*. More extensive data regarding division rates per 140 mm pot of 'LM300' in comparison with other *Lomandra longifolia* are presented in Table 2.

TABLE 2

| Species | Division per 140 mm Pot (Range) | Division per 300 mm Pot (Range) |
|---|---|---|
| 'LM300' | 7 to 10 | 24 to 32 |
| 'LM400' | 5 to 8 | 22 to 26 |

TABLE 2-continued

| Species | Division per 140 mm Pot (Range) | Division per 300 mm Pot (Range) |
|---|---|---|
| 'Katrinus' | 4 to 5 | 8 to 13 |
| 'Cassica' | 2 to 3 | 6 to 7 |
| Common *Lomandra** | 2 to 3 | 6 to 9 |

*Not subject to Australian Plant Breeders Rights
Reference; Abulk Nursery test plots at Windsor, New South Wales, AUSTRALIA
Divided between July, 6, 2001 and Dec. 15, 2001

Divisions of 'LM300' root quickly, within 3 to 4 weeks, as compared with 5 to 7 weeks for the parent *Lomandra longifolia* 'Katrinus'. The survival rate for 'LM300' division is 99% whilst *Lomandra longifolia* 'Katrinus' is approximately 85%. A more detailed comparison of division survival rate is provided in

TABLE 3

| Species | No. Of Divisions That Survived Out of 200 |
|---|---|
| 'LM300' | 198 |
| 'LM400' | 194 |
| 'Katrinus' | 170 |
| 'Cassica' | 159 |
| Common *Lomandra** | 163 |

*Not subject to Australian Plant Breeders Rights
Reference; Abulk Nursery test plots at Windsor, New South Wales, AUSTRALIA
Divided between July 6, 2001 and Dec. 15, 2001
50% sand and 50% peat was the potting mix used, with plants being divided into 90 mm × 50 mm × 50 mm tubes.

That which is claimed is:

1. A new and distinct variety of *Lomandra longifolia* plant named 'LM300', substantially as described and illustrated herein.

* * * * *

UNITED STATES PATENT AND TRADEMARK OFFICE

CERTIFICATE OF CORRECTION

PATENT NO. : PP 15,420 P3
DATED : December 14, 2004
INVENTOR(S) : Layt

It is certified that error appears in the above-identified patent and that said Letters Patent is hereby corrected as shown below:

Title page,
Item [56], References Cited, OTHER PUBLICATIONS, should include
-- UPOV-ROM Plant Variety Database, 2001/06, GTI Jouve Retrieval Software, Citation for Lomandra 'LM300' --

Column 6,
Line 6, should read -- *longifolia.* --

Signed and Sealed this

Seventh Day of June, 2005

JON W. DUDAS
*Director of the United States Patent and Trademark Office*